United States Patent [19]

Moore

[11] Patent Number: 4,457,709
[45] Date of Patent: Jul. 3, 1984

[54] HOLDING DEVICE FOR A DENTAL DOWEL PIN

[76] Inventor: Charles E. Moore, 420 Magazine St., Tupelo, Miss. 38801

[21] Appl. No.: 473,595

[22] Filed: Mar. 9, 1983

[51] Int. Cl.³ .............................................. A61C 19/00
[52] U.S. Cl. ........................................ 433/74; 24/550; 24/567
[58] Field of Search ................. 433/74, 53; 24/261 R; 248/175, 107, 153

[56] References Cited

U.S. PATENT DOCUMENTS

| 173,241 | 2/1876 | Schauble et al. | 248/175 |
| 517,545 | 4/1894 | Duckett | 24/261 R |
| 851,678 | 4/1907 | Levy | 24/261 R |
| 2,002,435 | 5/1935 | Dossey | 24/261 R |
| 2,155,496 | 4/1939 | Lane | 24/261 R |
| 3,469,316 | 9/1969 | Stern et al. | 433/74 |
| 3,553,839 | 1/1971 | Gores | 433/74 |
| 3,639,985 | 2/1972 | Pasko | 433/74 |

*Primary Examiner*—John J. Wilson

[57] ABSTRACT

The holding device of the present invention comprises an elongated wire rod of unitary construction having a lower straight section with a pointed end adapted for insertion into an impression material of a dental mold, an intermediate section having a wire coil adapted to grip a dowel pin and an upper section extending from the intermediate section and being angularly displaced therefrom such that upon compressing and releasing the upper section relative to the intermediate section the turns of the wire coil are spread open for inserting and releasably locking a dowel pin therein with the dowel pin being automatically aligned relative to said lower section.

6 Claims, 3 Drawing Figures

FIG. 2
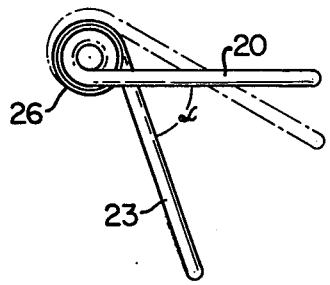
FIG. 1
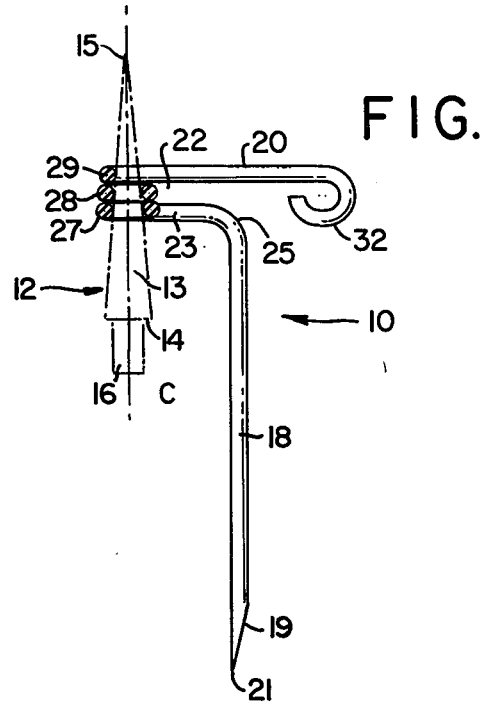
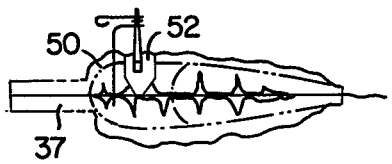
FIG. 3

HOLDING DEVICE FOR A DENTAL DOWEL PIN

This invention relates to dental dowel pins and more particularly to a holding device for positioning and holding a dowel pin in a dental mold of a tooth impression.

A dental dowel pin is an elongated member with a conical shape having a knurled stem adapted to be mounted in a die impression of a tooth replica. In the preparation of crowns, bridgework, false teeth and other prosthetic devices a model of the dental patients teeth is made by taking an impression of the necessary dentition to form a negative from which a positive is formed by inserting die casting material in the impression. The knurled stem of the dowel pin is inserted in the casting material before it hardens. When the replica of the tooth has solidified, the dowel pin is fixed permanently in position. A stone cast is then formed as a base for the die. A sawing operation is thereafter performed to make each die model removable from the cast. Precise dowel pin placement in the tooth impression is necessary for removing the tooth model and accurately relocating the model in the cast with respect to adjacent teeth. Various methods are now in use in dental laboratories and dental offices for holding and positioning the dowel pin in the die casting material. This is necessary so that after the dental die is separated from the stone cast it can be repositioned in the same position relative to the other teeth.

The present invention provides a simple, reliable and very inexpensive dowel pin holding device which allows the dentist or dental technician to readily position a dowel pin in any part of the dental impression material.

It is therefore the primary object of the present invention to provide a dental dowel pin holding device for positioning a dowel pin in a dental die impression of a tooth replica.

It is another object of the present invention to provide a dental dowel pin holding device which may be readily manipulated by a dentist or dental technical for setting the placement of the dowel pin in the dental die material.

It is yet another object of the present invention to provide a holding device for a dental dowel pin which is simple to use, inexpensive and highly reliable.

Other objects and advantages of the present invention will become apparent from the following detailed description of the invention when read in conjunction with the accompanying drawings of which:

FIG. 1 is a plan view of the dental dowel pin holding device of the present invention shown in combination with a dowel pin;

FIG. 2 is a top view of the dowel pin holding device of FIG. 1; and

FIG. 3 is a cross sectional view taken through a full mouth dental impression tray showing the holding device of the present invention holding a dowel pin in place within a mold cavity of a tooth impression.

Referring now to FIGS. 1-3 inclusive in which the dowel pin holder 10 of the present invention is shown with a dowel pin 12 mounted therein for placement in a die impression of a tooth replica. The dowel pin 12 is of conventional design having a conically tapered body 13 extending at one end from a base 14 and forming a relatively pointed apex 15 at the opposite end. A knurled cylindrical stem 16 extends from the base 14.

The holder 10 is an elongated single unit wire rod preferably of stainless steel having a lower section 18, an upper section 20 and and intermediate section 22. The lower section 18 is a straight section which has a flat beveled end 19 on one side thereof which terminates in a relatively sharp point 21. The intermediate section 22 has a straight portion 23 which is substantially perpendicular to the lower section 18 to form a substantially right angle elbow 25. The intermediate section 22 also includes a wire wound coil 26 which extends from the straight portion 23 and has at least two turns and preferably three turns 27, 28 and 29 with the first turn 27 coterminous with the straight portion 23 and with the last turn 29 coterminous with the upper section 20. The coil 26 is wound about an axis "C" which should lie substantially parallel to the lower section 18. The upper section 29 should form an included angle "d" of from about 50-85 degrees with the straight portion 23 of the intermediate section 22. The upper section 20 also has a free end 30 which is bent back or curled to form a loop 32. The loop 32 lies in a plane substantially parallel to the lower section 18.

The coil turns 27, 28 and 29 are preferably wound with each turn from turn 27 to turn 29 wound successively smaller in diameter than the previous turn i.e. turn 28 is slightly smaller in diameter than turn 27 and turn 29 is slightly smaller in diameter than turn 28. This arrangement results in an internal coil geometry which conforms to the conically tapered geometry of a conventional dowel pin.

The dowel pin 12 is inserted into the wire coil 26 by first pressing the loop 32 of the upper section 20 closer to the straight portion 23 of the intermediate section 22. This is accomplished by placing one finger such as a thumb on the loop 32 with another finger from the same hand such as the forefinger on the portion 23 and squeezing the two together. This action opens up the turns 27, 28 and 29. The phantom lines in FIG. 2 indicate the compressed position between the upper section 20 and the portion 23 of the intermediate section 22. With the turns of the wire coil spread open the conically tapered body 13 of the dowel pin 12 is easily inserted into the wire coil 26. The dowel pin 12 is then locked in place upon relieving the pressure between the loop 32 and the portion 23. This operates to securely engage the dowel pin 12 within the turns of the wire coil 26 and establishes concentricity between the central axis of the dowel pin and the coil axis "C" which assures axis parallelism between the dowel pin and the lower section 18.

The holder 10 may then be mounted into a dental mold 50 with the dowel pin 12 positioned in place about the dental cavity 52 of a tooth impression. This should preferably be done before the dental die casting material is poured into the cavity 52. As shown in FIG. 3 the pointed end 21 of the lower section 18 is inserted into the impression material 50 of a dental impression tray 37 such that the lower section is vertically oriented above the space 52 which defines an impression of a tooth. This space 52 is shown magnified in FIG. 3 for illustrative purposes. The holder 10 is pressed down until the knurled stem 16 is suspended within the cavity 52. The space or cavity 52 is then filled with die casting material to form the replica of the tooth. The disposition and alignment of the dowel pin is determined by the position and inclination of the lower section 18 of the holder 10. Once the lower section 18 is inserted into the dental impression material 50, the flat beveled end 19 prevents the lower section 18 from rotating during vibration or movement of the impression tray 37. The holder 10 may also be readily pulled out and repositioned if the accuracy of the first insertion is in doubt or if the dowel pin 12 was not desirably located.

I claim:

1. A dental holding device for holding an elongated tapered dowel pin of conical geometry in a secured position suspended above a cavity of a dental impression when making a positive replica of a tooth from such cavity comprising: an elongated wire rod of unitary construction having a lower straight section with a pointed end which is adapted to be inserted into the impression material adjacent the cavity, an intermediate section including a straight portion and a wire coil, with said wire coil having at least two turns for engaging the tapered body of the dowel pin with the central axis of the wire coil substantially aligned in parallel with said lower straight section and an upper section extending from said wire coil in a direction substantially transverse to said lower straight section and being angularly displaced from said straight portion of said intermediate section to form an included angle therewith of from about 50 to about 85 degrees such that by squeezing and releasing the upper section relative to said straight portion the dowel pin may be inserted and releasably locked in position within said wire coil.

2. A dental holding device as claimed in claim 1 wherein said pointed end of said lower straight section has a flatened surface on one side thereof.

3. A dental holding device as claimed in claim 2 wherein said upper section has a curled end in the form of a loop which lies in a plane substantially parallel with the plane of the lower section.

4. A dental holding device as claimed in claims 1 or 3 wherein said elongated wire rod forming said holding device is composed of stainless steel.

5. A dental holding device as claimed in claim 4 wherein said wire coil has at least three turns and wherein each successive turn from said lower section to said upper section is of slightly reduced diameter relative to the preceding turn.

6. A dental holding device as claimed in claim 5 wherein said straight portion of said intermediate section lies substantially perpendicular to said lower section.

* * * * *